US010583171B2

(12) United States Patent
Cohen-Kaminsky et al.

(10) Patent No.: US 10,583,171 B2
(45) Date of Patent: Mar. 10, 2020

(54) NMDAR ANTAGONISTS FOR THE TREATMENT OF DISEASES ASSOCIATED WITH ANGIOGENESIS

(71) Applicants: INSERM (Institut National de la Sante et de la Recherche Medicale), Paris (FR); Universite Paris-Sud, Orsay (FR)

(72) Inventors: Sylvia Cohen-Kaminsky, Le Plessis Robinson (FR); Sebastien Dumas, Le Plessis Robinson (FR); Gilles Bru-Mercier, Le Plessis Robinson (FR)

(73) Assignees: INSERM (Institut National de la Santé et de la Recherche Médicale), Paris (FR); Université Paris Sud, Orsay (FR)

( * ) Notice: Subject to any disclaimer, the term of this patent is extended or adjusted under 35 U.S.C. 154(b) by 0 days.

(21) Appl. No.: 15/779,369

(22) PCT Filed: Nov. 30, 2016

(86) PCT No.: PCT/EP2016/079340
§ 371 (c)(1),
(2) Date: May 25, 2018

(87) PCT Pub. No.: WO2017/093354
PCT Pub. Date: Jun. 8, 2017

(65) Prior Publication Data
US 2018/0318389 A1 Nov. 8, 2018

(30) Foreign Application Priority Data
Nov. 30, 2015 (EP) .................................... 15306894

(51) Int. Cl.
| | | |
|---|---|---|
| A61K 38/17 | (2006.01) | |
| A61K 31/135 | (2006.01) | |
| C12N 15/113 | (2010.01) | |
| A61K 31/13 | (2006.01) | |
| A61K 31/445 | (2006.01) | |
| A61K 45/06 | (2006.01) | |
| A61P 35/00 | (2006.01) | |
| A61K 31/451 | (2006.01) | |
| A61K 31/713 | (2006.01) | |
| A61K 39/395 | (2006.01) | |
| C07K 16/28 | (2006.01) | |
| A61K 31/662 | (2006.01) | |

(52) U.S. Cl.
CPC .......... *A61K 38/1787* (2013.01); *A61K 31/13* (2013.01); *A61K 31/135* (2013.01); *A61K 31/445* (2013.01); *A61K 31/451* (2013.01); *A61K 31/662* (2013.01); *A61K 31/713* (2013.01); *A61K 39/3955* (2013.01); *A61K 45/06* (2013.01); *A61P 35/00* (2018.01); *C07K 16/28* (2013.01); *C12N 15/113* (2013.01); *A61K 2300/00* (2013.01)

(58) Field of Classification Search
None
See application file for complete search history.

(56) References Cited

U.S. PATENT DOCUMENTS

| | | |
|---|---|---|
| 6,251,948 B1 | 6/2001 | Weber et al. |
| 2008/0145849 A1 | 6/2008 | North |
| 2008/0193503 A1 | 8/2008 | Hughes et al. |
| 2010/0130528 A1 | 5/2010 | Gant |
| 2010/0196354 A1* | 8/2010 | Morrell ................ A61K 31/165 424/130.1 |
| 2010/0216775 A1 | 8/2010 | Goel |
| 2014/0212421 A1* | 7/2014 | Hulmann-Cottier ........................ A61K 9/0043 424/135.1 |
| 2018/0000802 A1* | 1/2018 | Kim ..................... A61K 31/439 |

FOREIGN PATENT DOCUMENTS

| | | |
|---|---|---|
| EP | 2 264 035 A1 | 12/2010 |
| GB | 2 428 675 A | 2/2007 |
| WO | 2010/121973 A1 | 10/2010 |
| WO | 2014/187879 A2 | 11/2014 |

OTHER PUBLICATIONS

Williams et al.; "Ketamine Does Not Increase Pulmonary Vascular Resistance in Children with Pulmonary Hypertension Undergoing Sevoflurane Anesthesia and Spontaneous Ventilation"; Anesthesia and Analgesia, vol. 105, No. 6, Dec. 1, 2007, pp. 1578-1584.
Fares et al.; "Pulmonary hypertension: diagnostic and therapeutic challenges"; Therapeutics and Clinical risk Vlanagement, vol. 11, Aug. 1, 2015, pp. 1221-1233.

* cited by examiner

*Primary Examiner* — Sean McGarry
(74) *Attorney, Agent, or Firm* — W & C IP

(57) ABSTRACT

The present invention relates to an N-Methyl-D-aspartate (NMDA) receptor antagonist, for use in the treatment of diseases associated with angiogenesis such as tumor angiogenesis, ocular neovascular disease, Age-related macular degeneration (AMD).

8 Claims, 8 Drawing Sheets

Figure 1C:
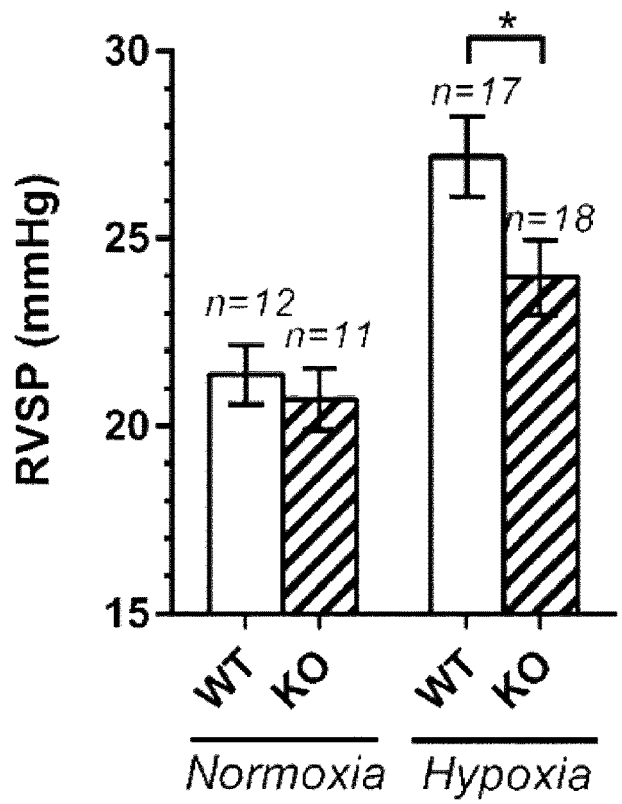

| | Control artery | Intimal lesion | Plexiform lesion |
|---|---|---|---|
| Membrane GluN1-associated immunogold particles (% of total) | 52.7 % | 51.0 % | 57.1 % |
| Synaptic-like contact length (% of total membrane length) | 2.2 % | 1.2 % | 2.2 % |
| Membrane GluN1-associated immunogold particles in synaptic-like contacts (% of total membranar GluN1) | 4.1 % | 7.7 % | 29.5 % |
| Concentration index of GluN1-associated immunogold particles in synaptic-like contacts (relative to control) | 1.0 | 3.5 | 7.1 |

Figure 1A

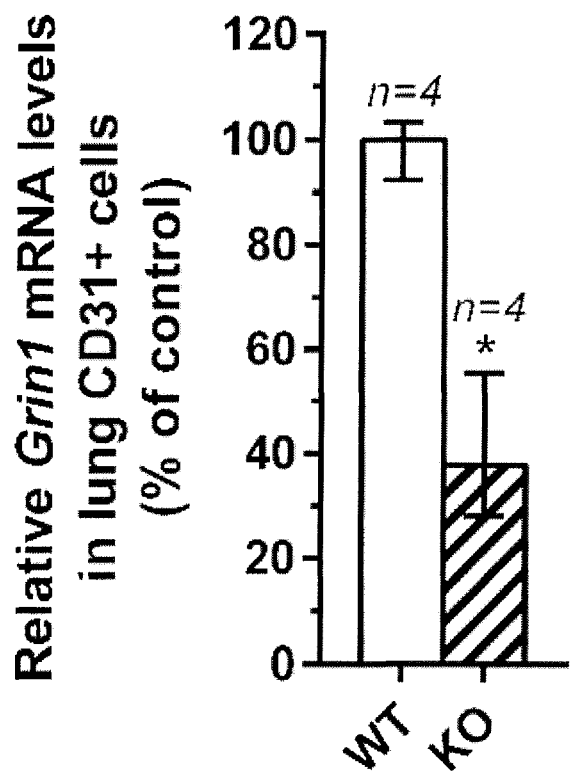

Figure 1B

NMDAR ANTAGONISTS FOR THE TREATMENT OF DISEASES ASSOCIATED WITH ANGIOGENESIS

FIELD OF THE INVENTION

The present invention relates to a method of treating disease associated with angiogenesis using an N-Methyl-D-aspartate receptor (NMDAR) antagonist. More specifically, it concerns use of an NMDA receptor antagonist, for the treatment of diseases associated with angiogenesis such as tumor angiogenesis, ocular neovascular disease, age-related macular degeneration (AMD).

BACKGROUND OF THE INVENTION

Angiogenesis is a biological process of generating new blood vessels into a tissue or an organ. Under normal physiological conditions, humans or animals undergo angiogenesis only in very specific restricted situations. For example, angiogenesis is normally observed in wound healing, fetal and embryonic development and formation of the corpus luteum, endometrium and placenta. It is widely accepted that new vessel growth is tightly controlled by many angiogenic regulators and the switch of the angiogenesis phenotype depends on the net balance between up-regulation of angiogenic stimulators and down-regulation of angiogenic suppressors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

In disease states where an imbalance of the angiogenic process is encountered, increasing or inhibiting angiogenesis could avert the corresponding body damages.

In many other situations, particularly when preventing or treating cancers is sought, a down-regulation of angiogenesis is desired.

Various substances are already known that prevent deregulation of angiogenesis, most of them inhibiting angiogenesis.

Until now, at least ten endogenous angiogenic inhibitors have been identified in the art. One such molecule is angiostatin, which consists of the plasminogen kringle domains I through IV. Also, apolipoprotein (a), one of the proteins having kringle structures, is a candidate for a novel angiogenesis inhibitor.

Several other kinds of compounds have been used to prevent angiogenesis. For example, Taylor et al. have used protamine to inhibit angiogenesis, although its toxicity limits its practical use as a therapeutic agent (Taylor et al., 1982, Nature, Vol. 297 : 307). Folkman et al. have disclosed the use of heparin and steroids to control angiogenesis (Folkman et al., 1983, Science, Vol. 221 : 719). Other agents which have been used to inhibit angiogenesis include ascorbic acid ethers and related compounds (Japanese Patent Kokai Tokkyo Koho No 58-131978). Also, a fungal product, fumagillin, is a potent angiostatic agent in vitro, as well as its synthetic derivative O-substituted fumagillin.

The United States Food and Drug Administration has granted the first marketing authorization for an anti-angiogenic therapeutic agent, which is termed bevacizumab. Bevacizumab is a humanized antibody directed against the angiogenic factor VEGF. Bevacizumab prevents the binding of VEGF to its effector receptor and has been initially used for treating colorectal cancer.

When taking into account the wide diversity of conditions or diseases that are caused by a deregulation of angiogenesis, or where deregulation of angiogenesis is involved, as well as the severity of several of these diseases, it flows that here is a high need in the art for the provision of novel therapeutically active substances that would allow circumventing physiological situations associated with a deregulation of angiogenesis, typically pathologically strong angiogenesis activity, and especially in cancer.

There is also a need in the art for new methods that would enable the screening of candidate substances for their angiogenesis regulation potency.

The N-methyl-D-Aspartate Receptor (NMDAR) is a ligand-gated and voltage-dependent channel belonging to the ionotropic glutamate receptor family[5]. It forms an heterotetrameric ion channel across the cell membrane and is composed of two GluN1 subunits (encoded by the GRIN1 gene), obligatory subunits to form functional NMDAR, containing a glycine or D-serine binding site, mainly associated to two GluN2 subunits either GluN2A, GluN2B, GluN2C or GluN2D subunits comprising the glutamate binding site, and modulating channel properties[5]. It is activated by both glutamate and glycine or D-serine, and in a context of membrane depolarization necessary to release magnesium ion acting as a channel blocker at resting potential. Conventional NMDAR has a major role in the central nervous system (CNS) as a key player of the excitatory synaptic neuronal communication[5]. Indeed, NMDAR distributes at the cell membrane in cell-cell contact sites either synaptic (defined by a close contact between neurons processes) or extrasynaptic sites (associated to close contacts mainly between neurons and microglial cells or astrocytes)[6]. Dysregulation of the NMDAR-mediated glutamatergic communication has been pointed out in many disorders in the CNS i.e. neurodegenerative disorders Alzheimer, Parkinson and Huntington diseases[7], but also depression, anxiety[8], schizophrenia, autism[9], stroke[10] etc. characterized by transcriptional and/or post-translational modification of NMDAR[10,11]. NMDAR has also been found outside the CNS: it is expressed by osteoclasts, osteoblasts, pancreatic beta cells, testis, keratinocytes, renal podocytes, immune cells, skeletal muscle, cardiomyocyte, etc. and also cerebral and aortic endothelial and smooth muscle cells[12-25]. On an other hand, vesicular glutamate transporters (Vgluts), allowing glutamate accumulation and fast release in a calcium-dependant way, a necessary event for fast glutamatergic communication, are also identified in peripheral tissues such as bones, islets of Langerhans, testes, pineal gland, intestines and stomach[26]. Studies have suggested a potential role of NMDAR in the development of chronic peripheral disorders such as osteoporosis[13] and type 2 diabetes mellitus[15], indicating that targeting peripheral NMDAR with a specific antagonist could be beneficial in these conditions. Some cancer cells can hijack the NMDAR to proliferate in an aberrant way[27]. The use of NMDAR-specific antagonists in animal models of cancer has shown dramatic improvements of the animal survival breaking tumor growth[28,29]. Additionally it has been demonstrated that NMDAR activation of cerebral or aortic endothelial cells contributes to blood-barrier opening, monocyte infiltration, reactive oxygen species production, apoptosis or proliferation[18-24]. In aortic smooth muscle cells, NMDAR activation triggers proliferation and MMP-2 synthesis[25].

SUMMARY OF THE INVENTION

In one aspect the invention provides an antagonist of the N-Methyl-D-aspartate receptor (NMDAR), for inhibiting angiogenesis.

In one embodiment, the antagonist of NMDAR according to the invention is for use in treating angiogenic dependent or angiogenic associated disease.

In one embodiment, said NMDAR antagonist may be a low molecular weight compound, e. g. a small organic molecule (natural or not).

In one embodiment, said antagonist is a competitive or a non-competitive or an uncompetitive antagonist of the NMDA receptor.

In another embodiment, the angiogenic dependent or angiogenic associated disease according to the invention is selected from tumor angiogenesis, ocular neovascular disease.

Typically, the antagonist according to the invention includes:

i. a small organic molecule;

ii. an anti-NMDAR antibody or antibody fragment that may partially or completely block NMDAR activation by glutamate (and glycine);

ii. a polypeptide that may partially or completely inhibit trafficking and anchoring at the cell membrane of the NMDAR.

In another aspect the invention provides an inhibitor of NMDAR expression for inhibiting angiogenesis.

DETAILED DESCRIPTION OF THE INVENTION

By using murine models of pulmonary arterial hypertension (PAH), the inventors took advantage of the significant differences in vascular NMDAR expression to explore the role of the major receptor of the excitatory synapses in the CNS in the pathophysiology of PAH, via intrinsic pulmonary vascular-lung mechanisms.

The inventors provide evidence that NMDAR activation promotes pulmonary arterial remodeling in PAH. Using different approaches, including in situ observations of dysregulated features of glutamatergic communication in human explanted PAH lungs, in vitro evidence of glutamate release from vascular cells and the role of NMDAR activation in vascular cell proliferation and angiogenesis, in vivo targeted knockout of NMDAR in endothelial or smooth muscle cells, they demonstrate a role for NMDAR activation in the vascular remodeling processes underlying pulmonary hypertension. Accordingly, the inventors show that blocking the NMDA receptor constitutes an alternative therapeutic axis in a disease associated with vascular cell proliferation and misguided and uncontrolled angiogenesis.

Therapeutic Methods and Uses

NMDAR Antagonist

The present invention provides methods and compositions (such as pharmaceutical compositions) for treating diseases associated with angiogenesis.

Thus an object of the invention is an antagonist of the N-Methyl-D-aspartate receptor (NMDAR), for inhibiting angiogenesis.

In one embodiment the antagonist of NMDAR according to the invention is for use in treating angiogenic dependent or angiogenic associated disease.

In one embodiment the NMDAR antagonist for use in treating disease associated with angiogenesis.

In one embodiment, the invention relates to a method of inhibiting angiogenesis in a subject in need thereof comprising administering an antagonist of NMDAR.

In one embodiment, the invention relates to a method of treating angiogenic dependent or angiogenic associated disease in a subject in need thereof comprising administering an antagonist of NMDAR.

By "antagonist" or "receptor antagonist" is meant a natural or synthetic compound that has a biological effect opposite to that of an agonist. An antagonist binds the receptor and blocks the action of a receptor agonist by competing with the agonist for receptor. An antagonist is defined by its ability to block the actions of an agonist.

The term "compound" as used throughout the specification includes but is not limited to: small organic molecule; antibody or antibody fragment that may partially or completely block NMDAR activation by glutamate (and glycine), a polypeptide or an inhibitor of NMDAR expression.

The expressions "N-Methyl-D-aspartate receptor" and "NMDA receptors" and "NMDAR" are used interchangeably herein and refer to human NMDAR protein. NMDA receptors consist of two glycine-binding GluN1 subunits encoded by eight splice variants of a single gene and two glutamate-binding GluN2 (A-D) subunits, arising from four genes (Traynelis S F et al Pharm Rev. 2010; 62(3)). NMDAR may also have a GluN3 (A-B) subunit Kehoe L A et al Neural Plast. 2013; 2013:145387) NMDA receptors uniquely require both glutamate and glycine as co-agonists for receptor activation (Johnson J W, et al Nature. 1987). Following channel opening, membrane depolarization is required to relieve the voltage-dependent Mg2+ block before ions can permeate the channel pore (Mayer M L, Nature. 1984).

The term "NMDA receptor antagonist" refers to a compound that reduces or block, the flow of cations (Na+, K+, Ca2+) through the NMDA receptor. The NMDA receptor antagonists comprise four categories of compounds: competitive antagonists, which bind to and block the binding site of the neurotransmitter glutamate; glycine antagonists, which bind to and block the glycine site; non-competitive antagonists, which inhibit NMDA receptors by binding to allosteric sites; and uncompetitive antagonists or channel blockers, which block the ion channel by binding to a site within it.

"Non-competitive antagonists" refer to compounds which require the binding of glycine and glutamate then said compound can bind to an allosteric site of the channel and block the flow of cations.

"Uncompetitive antagonists" refer to compounds which require the binding of an agonist of the NMDA receptor (e.g. glycine, glutamate) and the channel opening to access their blocking site. The uncompetitive channel blocker then becomes trapped within the NMDA receptor.

In one another embodiment, the antagonist of the NMDA receptor according to the invention, binds to the NMDA receptor and blocks the biological effect of glutamate (and glycine) on NMDAR. Such an antagonist can act by occupying the ligand binding site or a portion thereof of the NMDA receptor, thereby making the receptor inaccessible to its natural ligand so that its normal biological activity is prevented or reduced. To identify an antagonist able to block the biological effect between glutamate (and glycine) on NMDAR, a test based on the effect of the NMDAR antagonist candidate on the inhibition of angiogenesis (Matrigel assay) as explained in the examples (FIG. 1) may be used.

Alternatively, such an antagonist can act by binding directly to the intracellular domain of the receptor and inhibiting NMDAR trafficking to the cell membrane. Thus, a NMDAR antagonist may for instance block or inhibit NMDAR activation and/or trafficking to the cell membrane and/or anchoring at the cell membrane: e.g., blocking or inhibiting interaction of intracellular domain of the NMDAR with PDZ domain of scaffolding protein (like PSD95) and prevent its anchoring to the cell membrane (Tymianski M. et al Science. 2002 Oct. 25; 298(5594):846-50).

In one embodiment, the NMDAR antagonist is a low molecular weight compound, e. g. a small organic molecule (natural or not).

The term "small organic molecule" refers to a molecule of a size comparable to those organic molecules generally used in pharmaceuticals. The term excludes biological macromolecules (e. g. proteins, nucleic acids, etc.). Preferred small organic molecules, range in size up to about 5000 Da, more preferably up to 2000 Da, and most preferably up to about 1000 Da.

In a specific embodiment, the NMDA receptor antagonist according to the invention is a small organic molecule that binds any part of the NMDAR, including the channel part, and be able through allosteric effects, to modulate NMDAR activity.

Low molecular weight NMDAR antagonists are well known in the art. For example, low molecular weight NMDAR antagonists that may be used by the invention include, for example competitive NMDAR antagonists; glycine NMDAR antagonists; non-competitive NMDAR antagonists, and uncompetitive NMDAR antagonists or channel blockers as well as all pharmaceutically acceptable salts and solvates of said NMDAR antagonists, such as those described in the following patent publications: International and national Patent Publication Nos. WO09112797, WO9710240, WO2002072542, WO2006017409, WO2006113471; WO2006023957; WO2006020171, WO2007119098, WO2008137474, WO2009006437, WO2009061935; WO2009137843, WO2009092324, WO2009129181, WO20100033801, WO201013948, WO2010139483, WO201012213, WO2010060037, WO2010037533, WO2010033757, WO2012019106, U.S. Pat. Nos. 3,254,124, 6,916,816, 8,129,414, 7,786,140 US20080268071, EP2039354.

Additional non-limiting examples of low molecular weight NMDAR antagonists include any of the channel blockers (such as memantine; lanicemine, Remacemide amantadine; tiletamine; rimantadine, phencyclidine (PCP); PCP hydrochloride functional derivatives; dizocilpine MK-801, Argiotoxin 636, dextrorphan) since these channel blockers have also been described in Yamakura T, Neuroreport 1993; 4(6):687-90, Kashiwagi K, Mol Pharm 2002; 61(3):533-45 LePage K T Neuropharmacology 2005; 49(1): 1-16, Jin L, J Pharmacol Exp Ther 2007; 320(1):47-55, Burnashev N, Science 1992; 257(5075):1415-19.

Therefore, a specific example of low molecular weight NMDAR antagonist that can be used according to the present invention may be the (3,5-dimethyladamantan-1-amine) (also known as Memantine, Axura, Namenda, Ebixa and Mimetix) (Patent Publication No. U.S. Pat. No. 5,061,703, EP0392059) and which have the following structure:

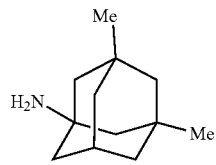 [SMILES: CC12CC3CC(C)(C1)CC(N)(C3)C2]

Another specific example of a low molecular weight NMDAR antagonist that can be used according to the present invention may be the [5R,10S]-[+]-5-methyl-10,11-dihydro-5H-dibenzo[a,d]cyclohepten-5,10-imine (also known as MK801, Dizocilpine (INN)) (Patent Publication No. U.S. Pat. No. 4,399,141, GB2061947) and which have the following structure:

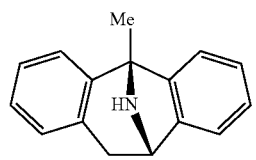 [SMILES: C[C@@]12N[C@@H](Cc3ccccc31)c1ccccc12]

Another specific example of a low molecular weight NMDAR antagonist that can be used according to the present invention may be the adamantan-1-amine (also known as Amantadine, Symmetrel) (Patent Publication No. U.S. Pat. No. 3,310,469, WO1992000066)

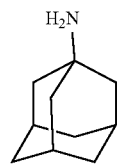

Another specific example of a low molecular weight NMDAR antagonist that can be used according to the present invention may be the 1-(1-phenylcyclohexyl)piperidine (also known as Phencyclidine, PCP, Sernyl)) (Patent Publication No. UK836083 and U.S. Pat. No. 3,097,136) and which have the following structure:

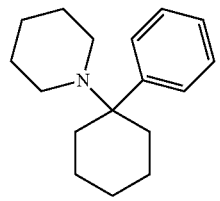 [SMILES: c1ccc(C2(N3CCCCC3)CCCCC2)cc1]

Another specific example of a low molecular weight NMDAR antagonist that can be used according to the present invention may be the (RS)-2-(2-Chlorophenyl)-2-(methylamino)cyclohexanone (also known as Ketamine and Ketamine hydrochloride) (Patent Publication No. U.S. Pat. No. 3,254,124) and which have the following structure:

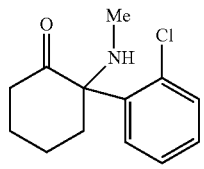 [SMILES: CNC1(c2ccccc2Cl)CCCCC1=O]

Another specific example of a low molecular weight NMDAR antagonist that can be used according to the present invention may be the 1(1-(1-aminoethyl)adamantane) (also known as rimantadine, Flumadine)) (Patent Publication No. U.S. Pat. Nos. 4,551,552 and 3,352,912) and which have the following structure:

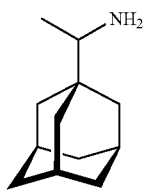

Another specific example of a low molecular weight NMDAR antagonist (noncompetitive antagonists) that can be used according to the present invention may be the 4-[2-(4-benzylpiperidin-1-yl)-1-hydroxypropyl]phenol (also known as ifenprodil, Vadilex; Dilvax; Creocral;)) (Patent Publication No. U.S. Pat. No. 3,509,164 and EP0109317) and which have the following structure:

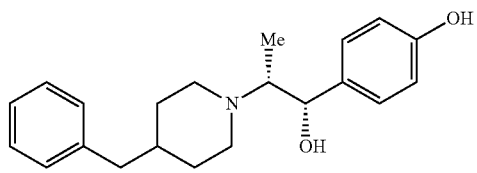 [SMILES: C[C@H]([C@@H](O)c1ccc(O)cc1)N1CCC(Cc2ccccc2)CC1]

Another specific example of a low molecular weight NMDAR antagonist (competitive antagonists) that can be used according to the present invention may be the 2-amino-5-phosphonopentanoïc acid (UPAC nomenclature) (also known as APV or AP5 or 2-amino-5-phosphonovaleric acid) which inhibits the binding site and which has the following structure

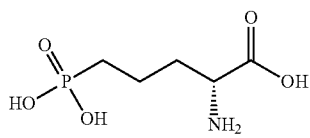

Additional non-limiting examples of low molecular weight NMDA receptor antagonists include but are not limited to any of the NMDA receptor antagonists described in Santagelo R M. et al. (Exp Opin. Ther Pat 22(11) 2012) or described in Strong KL and al ((Exp Opin. Ther Pat 24(12) 2014) or Mlodzic H et al (Exp Opin. Ther Pat 6(4), 1996) or Kolher M. et al (Exp Opin. Ther Pat 20(12), 2010) or Kulagowski JJ (Exp Opin. Ther Pat 6(10), 1996) which are herein incorporated by reference.

In one embodiment of the invention, the low molecular weight antagonist is non-competitive antagonist of the NMDA receptor. Examples of non-competitive antagonists include but are not limited to: ketamine, HU-211 or Dexanabinol, Rhynchophylline aptiganel or Cerestat or CNS-5 1102, ifenprodil, and/or analogs and/or functional derivatives thereof.

In another embodiment, the low molecular weight antagonist is an uncompetitive channel blocker of the NMDA receptor. Examples of uncompetitive antagonists of the NMDA receptor include but are not limited to: memantine; lanicemine, Remacemide amantadine; tiletamine; rimantadine, phencyclidine (PCP); PCP hydrochloride functional derivatives; dizocilpine MK-801, Argiotoxin 636, dextrorphan and/or analogs and/or functional derivatives thereof.

In another embodiment, said compound is memantine, or MK-801 and/or an analog and/or a functional derivative thereof.

In another embodiment, the low molecular weight antagonist is a competitive channel blocker of the NMDA receptor. Examples of competitive antagonists of the NMDA receptor include but are not limited to: AP5 (also known as APV), AP7, CPPene and Selfotel also known as CGS 19755), and/or analogs and/or functional derivatives thereof.

The term "Analog" refers broadly to the modification or substitution of one or more chemical moieties on a parent compound and may include functional derivatives, positional isomers, tautomers, zwitterions, enantiomers, diastereomers, racemates, isosteres or stereochemical mixtures thereof.

The term "Functional derivative" refers to a compound which possesses similar IC50 values and kinetics properties as MK-801 and memantine to NMDA receptor. The functional derivative of the invention possesses the capacity to suppress and/or decrease the angiogenesis. The functional derivative of the invention also may not target the central NMDAR, by not crossing the blood brain barrier after administration of the compound.

In a particular embodiment, the antagonist of the invention does not cross the blood brain barrier. Examples of such antagonists include but are not limited to AP5, also known as APV ((2R)-amino-5-phosphonovaleric acid; (2R)-amino-5-phosphonopentanoate) (Synaptic plasticity and learning: selective impairment of learning rats and blockade of long-term potentiation in vivo by the N-methyl-D-aspartate receptor antagonist AP5. Morris R G Journal of Neuroscience. 1989 September; 9(9):3040-57. PMID 2552039) and L-703,717 (Allosteric modulation of the glutamate site on the NMDA receptor by four novel glycine site antagonists. Grimwood S et al. Eur J Pharmacol. 1995 Aug. 15; 290(3): 221-6).

In another embodiment the NMDAR antagonist consists in an antibody or antibody fragment that may partially or completely block NMDA receptor activation by glutamate and glycine, or modulate its activity by binding to the channel site or any allosteric site of the receptor.

Antibodies against NMDAR are known in the art. Example of antibody-based NMDAR antagonists include those described in WO 2014187879 and include the well characterized antibody NMDA NR 1 Pan Antibody, mouse monoclonal, Novus biologicals, NB 300-118.

Additional antibody antagonists may be raised according to known methods by administering the appropriate antigen or epitope to a host animal selected, e.g., from pigs, cows, horses, rabbits, goats, sheep, and mice, among others. Various adjuvants known in the art may be used to enhance antibody production. Although antibodies useful in practicing the invention may be polyclonal, monoclonal antibodies are preferred. Monoclonal antibodies against NMDA receptor, may be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al, 1985, Monoclonal Antibodies and Cancer Therapy, Alan R. Liss, Inc., pp. 77-96). Alternatively, techniques described for the production of single chain antibodies (see, e.g., U.S. Pat. No. 4,946,778) may be adapted to produce anti-NMDAR, or anti-NMDAR single chain antibodies. NMDAR antagonists useful in practicing the present invention also include anti-NMDAR, or anti-NMDAR antibody fragments including but not limited to F(ab').sub.2 fragments, which may be generated by pepsin digestion of an intact antibody molecule, and Fab fragments, which may be generated by reducing the disulfide bridges of the F(ab').sub.2 fragments. Alternatively, Fab and/or scFv expression libraries may be constructed to allow rapid identification of fragments having the desired specificity to NMDA receptor.

Humanized anti-NMDAR and antibody fragments therefrom may also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In another embodiment the NMDAR antagonist consists in a polypeptide.

A polypeptide is a chain of amino acids linked by peptide bonds which contains between 10 and 100 amino acids.

As explain above the antagonist of the invention, may block NMDA receptor-protein interaction such as PSD-95 (Postsynaptic density-95 protein) which interacts with an intracellular domain of the NMDAR and prevents its anchoring to the cell membrane (Tymianski M. et al Science. 2002 Oct. 25; 298(5594):846-50).

In one embodiment the NMDAR antagonist consists in a polypeptide that may partially or completely inhibit trafficking or anchoring at the cell membrane of the NMDAR Specific examples of polypeptide targeting intracellular domain of the NMDAR that can be used according to the present invention include those described in the US20110097324; U.S. Pat. Nos. 8,071,548; 8,008,253; 7,846,897; US20120083449 US20100160240, U.S. Pat. No. 7,510,824.

Inhibitor of Expression

Another object of the invention is an inhibitor of NMDAR expression for inhibiting angiogenesis.

Inhibitors of NMDAR expression for use in the present invention may be based on antisense oligonucleotide constructs. Anti-sense oligonucleotides, including anti-sense RNA molecules and anti-sense DNA molecules, act to directly block the translation of NMDAR mRNA by binding thereto and thus preventing protein translation or increasing mRNA degradation, thus decreasing the level of NMDAR proteins, and thus activity, in a cell. For example, antisense oligonucleotides of at least about 15 bases and complementary to unique regions of the mRNA transcript sequence encoding NMDAR or may be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Specific examples of siRNAs targeting NMDAR that can be used according to the present invention include those described in the US Patent Publication No. U.S. Pat. No. 8,372,817.

Small inhibitory RNAs (siRNAs) may also function as inhibitors of NMDAR expression for use in the present invention. NMDAR gene expression may be reduced by contacting the pathological site with deregulated angiogenesis like tumor, cell with a small double stranded RNA (dsRNA), or a vector or construct causing the production of a small double stranded RNA, such that NMDAR expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes may also function as inhibitors of NMDAR expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of NMDAR mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using, e.g., ribonuclease protection assays.

Both antisense oligonucleotides and ribozymes useful as inhibitors of NMDAR expression may be prepared by known methods. These include techniques for chemical synthesis such as, e.g., by solid phase phosphoramadite chemical synthesis. Alternatively, anti-sense RNA molecules may be generated by in vitro or in vivo transcription of DNA sequences encoding the RNA molecule. Such DNA sequences may be incorporated into a wide variety of vectors that incorporate suitable RNA polymerase promoters such as the T7 or SP6 polymerase promoters. Various modifications to the oligonucleotides of the invention may be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing NMDAR. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One may readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus may be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus may integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus may also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, may express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid may be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Method for Inhibiting Angiogenesis

Another object of the invention relates to a method for inhibiting angiogenesis or method for treating disease associated with angiogenesis comprising administering a subject in need thereof with a therapeutically effective amount of an antagonist or inhibitor of expression as described above.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "patient" or "patient in need thereof", is intended for a human or non-human mammal affected or likely to be affected with a pathological condition or disease involving deregulated angiogenesis. By a "therapeutically effective amount" of the antagonist or inhibitor of expression as above described is meant a sufficient amount of the antagonist or inhibitor of expression to treat disease associated with angiogenesis at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific therapeutical agent employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

Antagonists of the invention may further be identified by the screening methods described in the state of the art. The screening methods of the invention may be carried out according to known methods.

The screening method may measure the binding of a candidate compound to the NMDA receptor, or to cells or membranes bearing the NMDAR receptor, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist or agonist). Further, screening methods may test whether the candidate compound results in a signal generated by an antagonist of the receptor, using detection systems appropriate to cells bearing the NMDA receptor. Antagonists may be assayed in the presence of a known agonist (e.g., glutamate or NMDA) and co-agoniste (glycine, D-serine) and an effect on activation by the agonist by the presence of the candidate compound is observed. Competitive binding using known agonist such glutamate (or glycine) is also suitable.

Disease Associated With Angiogenesis

Thus an object of the invention is an antagonist of the N-Methyl-D-aspartate receptor (NMDAR), for inhibiting angiogenesis.

In one embodiment the antagonist of NMDAR according to the invention is for use in treating angiogenic dependent or angiogenic associated disease.

In the context of the present invention, the term "disease associated with angiogenesis" means a disease associated with a persistent, unregulated angiogenesis. The conditions or diseases that are concerned are those for which angiogenesis is pathological and should be reduced or blocked.

Persistent, unregulated angiogenesis occurs in a multiplicity of disease states, including tumor growth and tumor metastasis, and supports the pathological damage seen in these conditions. The diverse pathological states that are due to unregulated angiogenesis have been grouped together as angiogenic dependent or angiogenic associated diseases or conditions.

One example of a disease mediated by angiogenesis is ocular neovascular disease, which is characterized by invasion of new blood vessels into the structure of the eye such as the retina or the cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissues beneath the retinal pigment epithelium. Angiogenic damage is also associated with diabetic retinopathy, retinopathy of prematurity, corneal graft rejection, neovascular glaucoma, and retrolental fibroplasias. Other diseases associated with corneal neovascularization include, but are not limited to, epidemic keratoconjunctivitis, Vitamin A deficiency, contact lens overwear, atopic keratitis, superior limbic keratitis, pterygium kreatitis sicca, sjogrens, acne rosacea, phylectenulosis, syphilis, mycobacterial infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, rheumatois arthritis, systemic lupus, polyarteritis, Wegener's sarcoidiosis, scleritis, Stevens-Johnson disease, pemphigoid, radial keratotomy and corneal graft rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobaterial infections, Lyme's disease, systemic lupus erythematosis, retinopathy of prematurity, Eale's disease, Bechet's disease, infections causing retinitis or choroiditis, presumed ocular histoplasmosis, Best's disease, myopia, optic pits, Stargardt's disease, pars planitis, chronic etinal detachment, hyperviscosity syndromes, toxoplasmosis, trauma and post-laser complications. Other diseases include, but are not limited to, diseases associated with rubeosis, which causes neovascularisation of the angle, and diseases caused by abnormal proliferation of fibrovascular or fibrous tissue including all forms of proliferative vitreoretinopathy.

Another disease in which angiogenesis is involved is rheumatoid arthritis. The blood vessels in the synovial lining of the joints undergo angiogenesis. In addition to forming new vascular networks, the endothelial cells release factors and reactive oxygen species that lead to panus growth and cartilage destruction. The factors involved in angiogenesis may actively contribute to, and help maintain, the chronically inflamed state of rheumatoid arthritis.

Angiogenesis is also involved in osteoarthritis. The activation of the chondrocytes by angiogenic-related factors contributes to the destruction of the joint.

Also, deregulation of angiogenesis is the cause of hemangioma, which is one of the most frequent angiogenic diseases in childhood.

Deregulation of angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasias can be a detrimental side effect of surgical procedures and may be caused or exacerbated by angiogenesis. Adhesions are a frequent complication of surgery and lead to problems such as small bowel obstruction.

Of particular importance, both primary and metastatic tumors need to recruit angiogenic vessels for their growth. If this angiogenic activity could be repressed or eliminated, then the tumor would not grow. Thus, angiogenesis is prominent in solid tumor formation and metastasis.

Angiogenic factors have been found associated with various solid tumors such as rhabdomyosarcomas, retinoblastoma, Ewing sarcoma, neuroblastoma, osteosarcoma as well as with colorectal cancer. Tumors in which angiogenesis is important include solid tumors, and benign tumors such as acoustic neurona, neurofibroma, trachoma and pyogenic granulomas. Further, angiogenesis has been associated with blood-born tumors such as leukemias, any of various acute or chronic neoplastic diseases of the bone marrow in which unrestrained proliferation of white blood cells.

Angiogenesis is important in two stages of tumor metastasis. The first stage where angiogenesis is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand.

As illustrated hereabove, deregulation of angiogenesis is the cause of a wide variety of pathological conditions or disease states.

Pharmaceutical Compositions

The antagonist or inhibitor of expression of the invention may be combined with pharmaceutically acceptable excipients, and optionally sustained-release matrices, such as biodegradable polymers, to form therapeutic compositions for use in the treatment of pathological conditions with deregulated angiogenesis as illustrated here above.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, may be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The antagonist or inhibitor of expression of the invention may be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, histidine, procaine and the like.

The carrier may also be a solvent or dispersion medium containing, for example, water, ethanol, polyol (for example, glycerol, propylene glycol, and liquid polyethylene glycol, and the like), suitable mixtures thereof, and vegetables oils. The proper fluidity may be maintained, for example, by the use of a coating, such as lecithin, by the maintenance of the required particle size in the case of dispersion and by the use of surfactants. The prevention of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions may be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions are administered in a manner compatible with the dosage formulation and in such amount as is therapeutically effective. The formulations are easily administered in a variety of dosage forms, such as the type of injectable solutions described above, but drug release capsules and the like may also be employed.

For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which may be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The antagonist or inhibitor of expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses may also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will further be illustrated in view of the following figures and examples.

FIGURES

FIG. 1: Activation of endothelial cell NMDAR contributes to vascular remodeling in the development of pulmonary hypertension.

(a) The table summarizes quantitation of total membrane GluN1 i.e NMDAR available for activation, in endothelial cells and also specifically in synaptic-like contact (defined as a close contact <70 µm between two endothelial cells without junctions). A concentration index of GluN1 in the synaptic-like contacts was determined calculating the ratio of the percent of membrane GluN1 in these synaptic-like contacts divided by the percent of synaptic contact length.

(b) Quantitative RT-PCR analysis of GRIN1 gene expression from total RNA of CD31+ cells and CD31− cells isolated from the lungs of wild-type mice (n=4) and knocked-out mice (n=4) for the NMDAR in ECs showing efficiency of Grin1 knockout in ECs. Grin1 gene expression is normalized to Actinb gene expression. Values are normalized to those of WT mice.

(c) Right Ventricular Systolic Pressure (RVSP) measurement in wild-type (n=11-12) and knocked-out mice for the NMDAR in ECs (n=17-18) after 3 weeks of normoxia or chronic hypoxia ($FiO_2$: 10%).

(d) Ratio of right ventricular weight to left ventricular plus septum weight (Fulton index) measured in wild-type (n=12) or knocked-out mice for the NMDAR in ECs (n=19-20) after 3 weeks of normoxia or chronic hypoxia ($FiO_2$: 10%). Same experiment as in c).

(e) Morphometric analysis of pulmonary vessels in wild-type or knocked-out mice for the NMDAR in ECs after 3 weeks of normoxia or chronic hypoxia ($FiO_2$: 10%). Same experiment as in c) and d). Pulmonary vessels are divided in 4 groups depending on the external vessel diameter (less than 30 µm, from 30 µm to 50 µm, from 50 µm to 75 µm and from 75 µm to 125 µm). 100 vessels were analyzed for each group (20 vessels per group and per mice). Each vessel was classified as a non muscularized vessel (VWF+, α-smooth muscle actin-), partially muscularized vessel (VWF+, α-smooth muscle actin+/−), and fully muscularized vessel (VWF+, α-smooth muscle actin+).

(f) Measurement of control hPMVEC proliferation (BrdU incorporation), after exposure to VEGF-A (10 ng·$m^{-1}$) in absence or presence of incremental concentrations of NMDAR antagonists MK-801 or memantine (MMT) (both from 10 µM to 100 µM). Values are normalized to those of non-stimulated cultures. Data are means of eight replicates and the graphs are representative of three independent experiments.

Figure 2A:
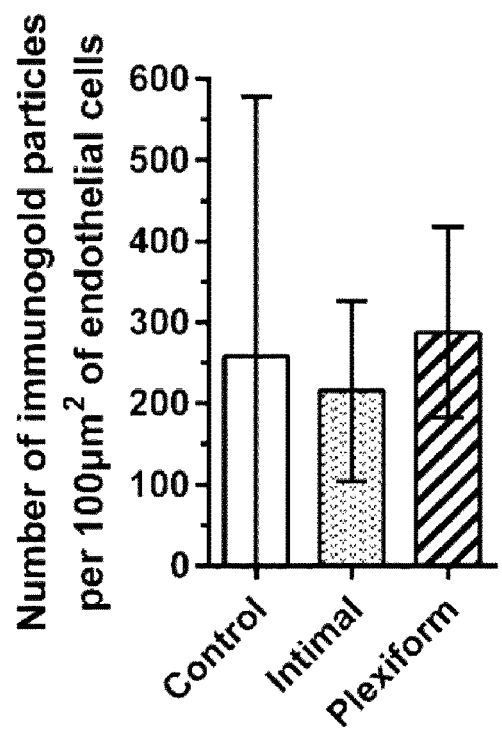
Figure 2B:
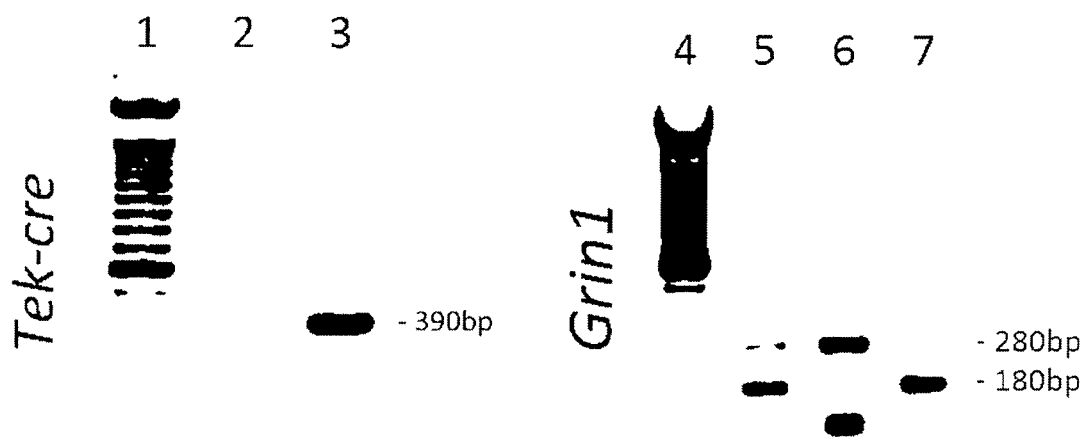
Figure 2C:
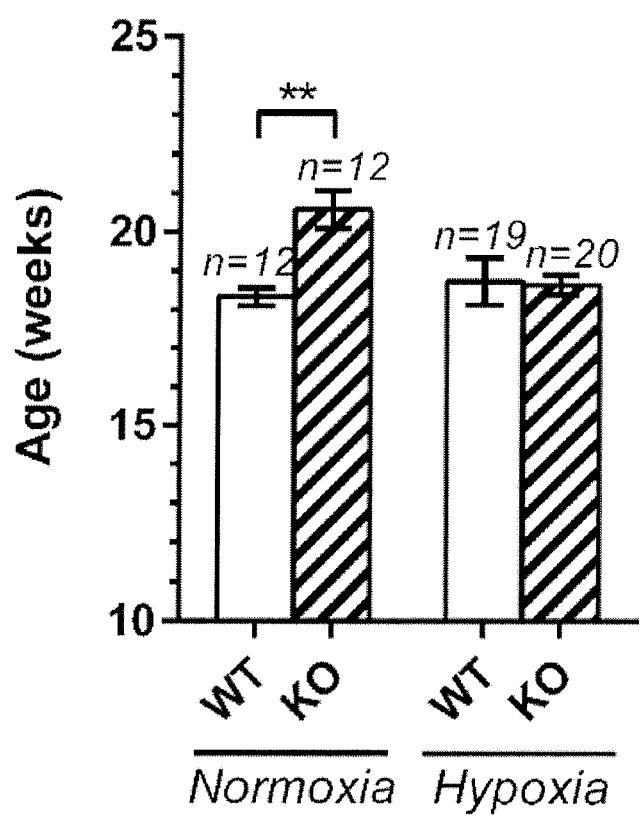
Figure 2D:
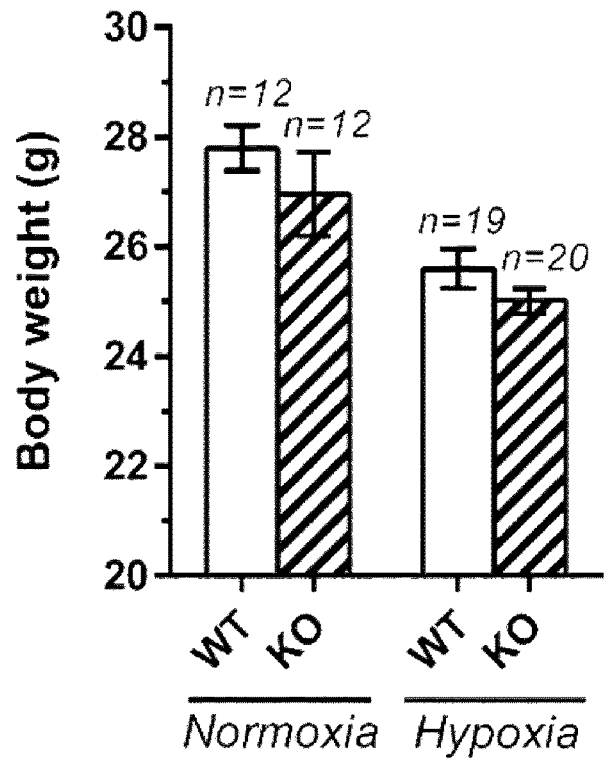
Figure 2E:
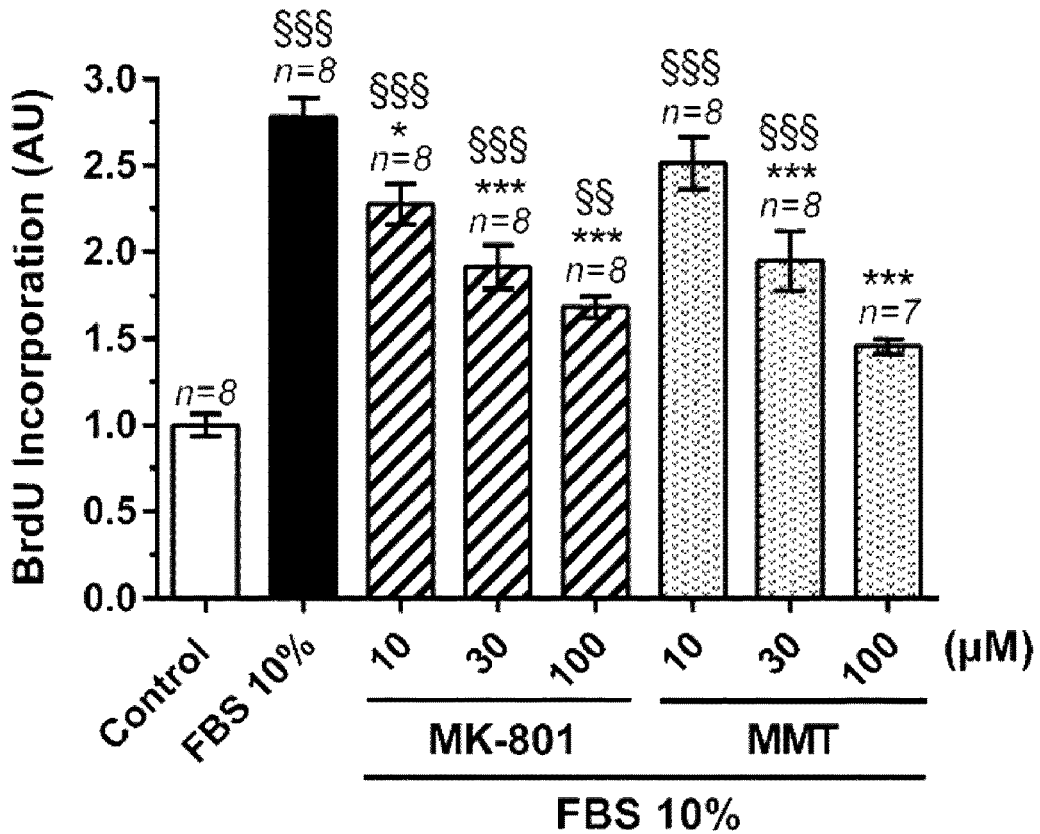
Figure 2F:
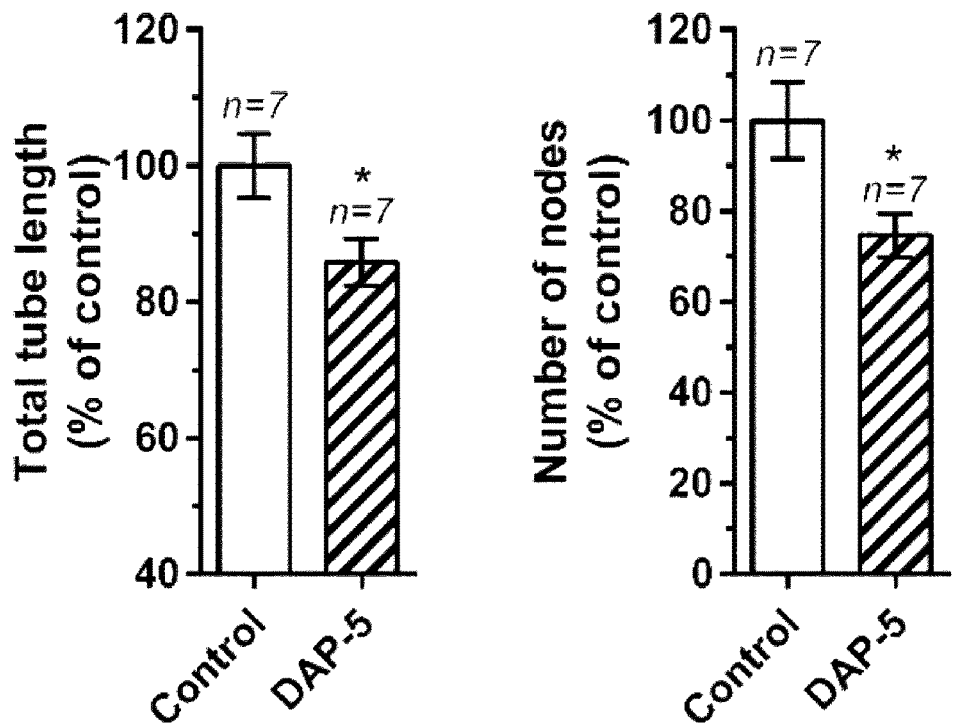

(g) In vitro angiogenesis experiments using control hPMVEC in the Matrigel™ assay with or without 100 µM NMDAR antagonist (+)-MK-801 maleate. On the left automatic quantification of total tube length and total number of nodes using the "Angiogenesis analyzer" plugin from ImageJ software on a total of 7-8 images (1 image/replicate, each image covering nearly all the well area). Values are expressed as percent of control. On the right representative transmitted light microscopy images (upper and middle images) and associated skeletonized images (lower images) of three experiments are shown. Scale bar 500 µm. Similar results were obtained using 50 µM DAP-V (FIG. 2f).

(h) In vitro angiogenesis experiments in a coculture assay using control hPASMC and hPMVEC. hPMVEC were seeded on the top of the confluent hPASMC layer with or without incremental concentrations of NMDAR antagonist (+)-MK-801 maleate ranging from 10 to 100 µM, in six replicate cultures for each concentration. CD31 labelling was used to visualize the tube network after 15 days of co-culture.

Statistical significance was determined by Mann Whitney test (b), regular two-way ANOVA followed by Bonferonni's test (c-e), one-way ANOVA followed by Bonferonni's multiple comparison test (f, h) or Student's t test (g). *$p<0.05$, ***$p<0.001$ compared to WT/control (b-e, g, h) or $^{§§§}$ $p<0.001$ compared to control, *$p<0.05$, ***$p<0.001$ compared to VEGF (f). Values are median±interquartile range (b) or mean±SEM (c-h).

FIG. 2: Supplementary figures about activation of endothelial cell NMDAR contributes to vascular remodeling in the development of pulmonary hypertension.

(a) Quantitation of total GluN1-associated immunogold particles per 100 $µm^2$ of endothelial cells in arteries from a control patient, and in an intimal lesion and plexiform lesion from a PAH patient.

(b) Genotyping of Tek-creXGrin1 mice. For the Cre gene, the first agarose gel shows a band at the expected molecular weight: lane 1 is the DNA ladder, lane 2 is a WT mice (absence of band) and lane 3 is a recombinant mice (presence of a band at 390 bp). For the floxed Grin1 gene, the second agarose gel shows bands at expected molecular weights: lane 4 is the DNA ladder, lane 5 is a hemizygous mice (two bands at 180 bp and 280 bp), lane 6 is a homozygous mice (floxed Grin1 band only, at 280 bp) and lane 7 is a WT mice (WT Grin1 band only, at 180 bp).

Figure 1D:
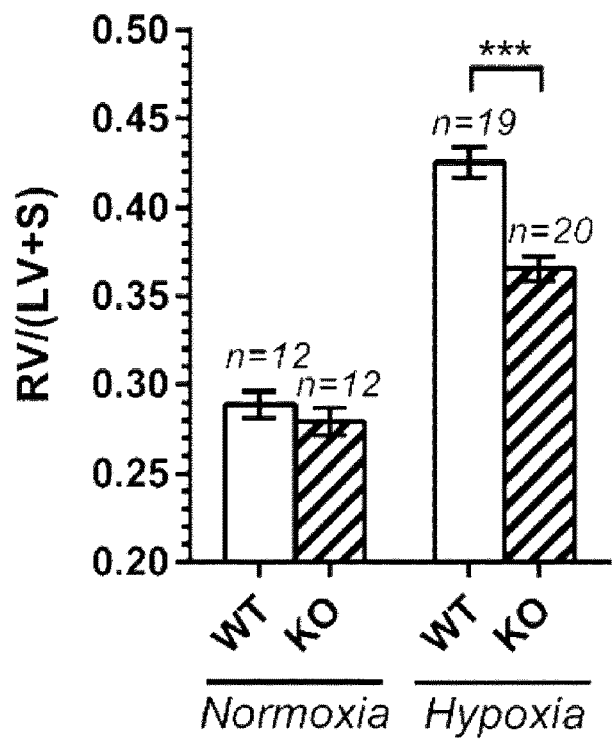
Figure 1E:
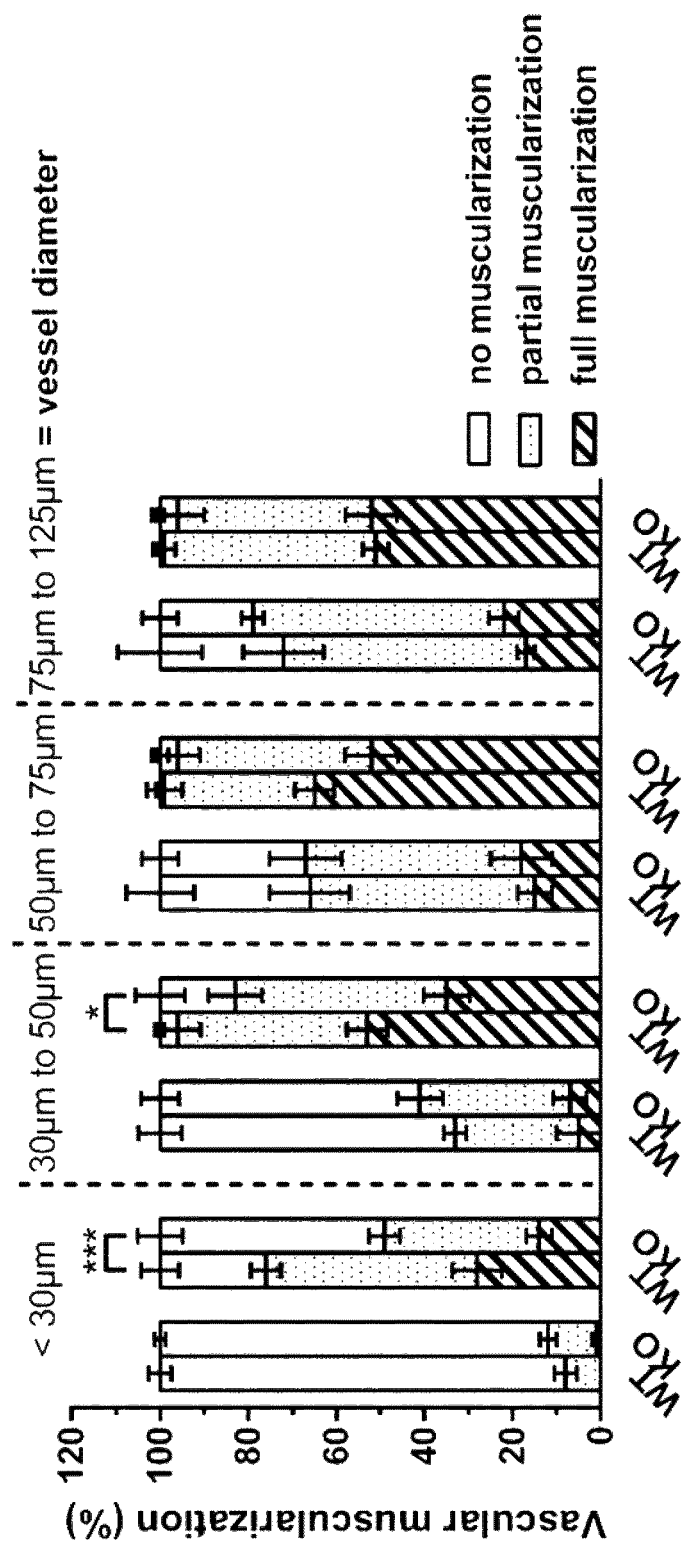

(c) Age of wild-type (n=12) and knocked-out mice for NMDAR in ECs (n=19-20) after 3 weeks of normoxia or chronic hypoxia, that were used in the experiment depicted in FIG. 1c-e.

(d) Body weight of wild-type (n=12) and knocked-out mice for NMDAR in ECs (n=19-20) after 3 weeks of normoxia or chronic hypoxia that were used in the experiment depicted in FIG. 1c-e.

(e) Measurement of control hPMVEC proliferation (BrdU incorporation) after exposure to fetal bovine serum (FBS 10%) in absence or presence of NMDAR antagonists MK-801 or memantine (MMT) (both from 10 μM to 100 μM). Values are normalized to those of non-stimulated cultures. Data are means of six replicates and the graph is representative of three independent experiments.

(f) In vitro angiogenesis experiments using control hPMVEC in the Matrigel™ assay with or without 50 μM NMDAR antagonist DAP-V. Automatic quantification of total tube length and total number of nodes using the "Angiogenesis analyzer" plugin from ImageJ software on a total 7-8 images (1 image/replicate, each image covering nearly all the well area). Values are expressed as percent of control. Data are representative of two independent experiments.

(g) In vitro angiogenesis experiments in a coculture assay using control hPASMC and hPMVEC with or without incremental concentrations of NMDAR antagonist (+)-MK-801 maleate ranging from 10 to 100 μM, in six replicate cultures for each concentration. Different quantification method of the same experiment as in FIG. 1h. Automatic quantification of total tube length represented by CD31 staining area performed using AngioQuant software. Values are expressed as percent of control.

Statistical significance was determined by Kruskal Wallis test followed by Dunn's multiple comparison tests (a), regular two-way ANOVA followed by Bonferonni's test (c, d), one-way ANOVA followed by Bonferonni's multiple comparison test (e, g) or Student's t test (f). *$p<0.05$, $p<0.01$, *$p<0.001$ compared to WT/control (a, c, d, f, g) or $^{\S\S}$ $p<0.01$, $^{\S\S\S}$ $p<0.001$ compared to control, *$p<0.05$, ***$p<0.001$ compared to FBS 10% (e). Values are median±interquartile range (a) or mean±SEM (c-d, f-h).

EXAMPLE

Material & Methods
Cell Culture

Experiments requiring cells were performed on human pulmonary arterial smooth muscle cells (hPASMC, LONZA, Basel, Switzerland), human pulmonary microvascular endothelial cells (hPMVEC, LONZA, Basel, Switzerland), between P4 and P7, both from healthy non-smoker and non-alcoholic donors and on primary culture of hippocampal neurons from rat fetuses.

For hPASMC culture, 250 000 cells were seeded in T75 flasks (BD Falcon, CORNING, Tewksbury, Mass., USA) and grown in the SmGm2 complete medium containing SmBm basal medium and also basic fibroblast growth factor, epidermal growth factor, insulin and gentamycin/amphotericin 1× (all from LONZA, Basel, Switzerland).

For hPMVEC culture, 375 000 cells were seeded in T75 flasks (BD Falcon, CORNING, Tewksbury, Mass., USA) and grown in the EGM2-MV complete medium containing EBM2 basal medium and basic fibroblast growth factor-b, epidermal growth factor, vascular endothelial growth factor, hydrocortisone, ascorbic acid, insulin-like growth factor and gentamycin/amphotericin 1× (all from LONZA, Basel, Switzerland).

All cells were cultured at 37° C. in a humidified atmosphere of 5% $CO_2$ and 95% air.

Angiogenesis Assays

Matrigel assays were performed on μ-slide angiogenesis (IBIDI, Martinsried, Germany). 100 μL of phenol-red free matrigel matrix (BD, Franklin lakes, N.J., USA) were put in each wells and slides were incubated during 30 min at 37° C. Then, 50 μL of EGM2-MV medium with our without NMDAR antagonists (100 μM (+)-MK-801 maleate or 50 μM DAP-V, both from ABCAM BIOCHEMICALS, Cambridge, UK) were added on matrigel gels during 1 hour. 3500 hPMVEC were seeded in each well in presence or absence of NMDAR antagonists. After 4 hours, bright-field images of capillary-like structures were captured using Eclipse 80i microscope coupled to Nis Elements BR2.30 software. Images were then automatically analyzed with "Angiogenesis analyzer" plugin for ImageJ software resulting in total tube length and total number of nodes determination.

For the hPASMC/hPMVEC co-culture model of angiogenesis, 20000 PASMC were seeded on glass coverslips in a 12-well plate (CORNING, Tewksbury, Mass., USA) and cultured until confluence in SmGm2 complete medium. After reaching high confluence, 80000 PMVEC were seeded on the top of the PASMC layer switching the medium from SmGm2 complete medium to a modified EGM2-MV complete medium containing 2% FBS with our without NMDAR antagonist MK-801 at 0 μM, 10 μM, 30 μM or 100 μM MK-801 (6 replicates per condition). Medium was changed every 2 to 3 days and after 15 days of co-culture, cells were fixed and CD31 was stained. After staining, 5×5 images of each coverslip were captured using mosaic mode of acquisition with a Zeiss Axio Observer Z1 microscope coupled to Axiovision 4.8 software (both from CARL ZEISS, Oberkochen, Germany). Images were analysed using ImageJ software in order to calculate the CD31 staining area to the total cell area ratio. This ratio was further named as the total tube length. Automatic quantitation was also achieved using AngioQuant software[70] to determine total tube length.

Animal Models

All animals were used in strict accordance to the European Union regulations (Directive 2010/63/UE) for animal experiments and complied with our institution's guidelines for animal care and handling. All animals were maintained in a temperature and humidity-controlled room with a 12 h/12 h light/dark cycle with access to a standard rat chow and water ad libitum. Following procedures performed on rats or mice, were approved by the ethical committee CEEA26 (Animal experimentation ethic committee no 26") and the French ministry of higher education and research.

The transgenic mice strain used are B6.129S4-Grin1$^{tm2Stl}$/J (further named as GRIN1$^{fl/fl}$ mice), (from JACKSON LABORATORY, Bar Harbor, Me., USA) and B6.Cg-Tg(Tek-cre/ERT2)1Arnd/ArndCnrm (further named as Tek-cre mice) (EUROPEAN MOUSE MUTANT ARCHIVE, CNR Monterotondo, Monterotondo, RM, Italy). Briefly, GRIN1$^{fl/fl}$ mice were crossed with Tek-cre mice. For NMDAR knocked out in endothelial cells, experiments were performed on male Tek-crexGRIN1$^{fl/fl}$ mice and male Tek-cre mice were used as controls after 5 weeks of Tamoxifen-containing chow (HARLAN LABORATORIES, Indianapolis, Ind., USA) administration followed by 1 week of standard chow. Pulmonary hypertension was induced exposing mice to 3 weeks of hypoxia (10% $FiO_2$). Then, mice were submitted to anesthesia induced by inhalation of isoflurane 3% mixed with air and maintained decreasing isoflurance concentration between 1% and 1.5%. Right-heart catheterization and organ processing were performed using standard methods. The heart was taken out the 30 thoracic cage, auricles were removed and right ventricles were separated from left ventricles associated to septa. The weight of each part was measured and the ratio of the right ventricle weigh to the left ventricle with septum weigh was calculated for each mouse. Lungs were processed inflating them with 10 mL of a mixture of saline and OCT 1/1 ratio (Shandon™ Cryomatrix™, THERMOFISCHER SCIENTIFIC). Ventricles and inflated lungs were then frozen in cooled isopentane (VWR) and stored at −80° C.

For morphometric analysis of pulmonary arteries, 6 μm thick sections of mouse lungs were cut with a cryomicrotome (LEICA MICROSYSTEMS). Sections were allowed to dry during 1 hour under a hood. Then, they were fixed in cold acetone for 10 minutes. 10% goat serum plus 5% mouse serum were incubated for 1 hour to prevent unspecific binding of antibodies. Anti-VWF and 10 Anti-alpha smooth muscle cell-FITC antibodies were incubated in presence of 2% mouse serum during 1 hour at room temperature. A negative control was performed omitting primary antibodies. The secondary antibody was incubated during 30 minutes in presence of 2% mouse serum. DAPI (LIFE TECHNOLOGIES) diluted at 1/500 was incubated during 1 minute. Glass slides were finally mounted using Dako Fluorescent mounting 15 medium (DAKO). Sections were then analyzed using Eclipse 80i microscope coupled to Nis Elements BR2.30 software (NIKON). For statistical analysis performed on mouse lungs, intrapulmonary arterioles were divided in four groups based on their external diameter: less than 30 μm, from 30 μm to 50 μm, from 50 μm to 75 μm and from 75 μm to 125 μm. 20 arterioles per 20 category identified with the VWF staining were qualified as non muscularized, partially muscularized or fully muscularized based on the alpha smooth muscle actin staining. 5 mice/group were included in the study.

Results

Activation of Smooth Muscle Cell NMDAR Contributes to the Vascular Remodeling Occurring During PH Development.

NMDAR activation has been previously associated to aortic smooth muscle cell proliferation depending of MAPK and PI3K signaling pathway activation[25]. Besides, NMDAR activation has been pointed out as an important component of the aberrant proliferation of cancer cells and PAH PASMCs exhibit a cancer-like phenotype. To determine a potential role of PASMC NMDAR in progressive vascular remodeling and subsequent PAH, we have developed knockout (KO) mice for NMDAR, with targeted deletion of the Grin1 gene in SMCs using a Cre/Lox approach. Grin1 gene expression was clearly reduced in pulmonary arteries from KO mice compared to wild-type (WT) mice indicating efficient genetic recombination. Age-matched KO and WT male mice were exposed to 3 weeks normoxia or hypoxia ($FiO_2$ 10%) in order to induce experimental PH. Normoxic KO and WT mice didn't show any differences in right ventricular systolic pressure (RVSP) and right cardiac hypertrophy (Fulton index) opposite to hypoxic KO mice presenting significantly lower RVSP and Fulton index than hypoxic WT mice. This was associated to a decreased muscularization of small pulmonary arterioles (<50 μm external diameter) in hypoxic KO mice compared to WT mice. Interestingly, a decreased muscularization of large arteries (from 75 μm to 125 μm external diameter) was also noticed in KO mice compared to WT mice independently of hypoxia exposure, suggesting a role for NMDAR in physiological smooth muscle cell coverage of pulmonary arteries. No significant difference in body weight was noticed between KO and WT mice in both normoxia and hypoxia. As proliferation of hPASMCs is a crucial determinant of vascular remodeling associated to increased pulmonary vascular resistance and pressure, we analyzed the role of NMDAR activation in hPASMCs proliferation. Using two non-structurally related NMDAR uncompetitive antagonists, MK-801 and memantine (MMT), we show dose-dependent inhibition of proliferation induced by PDGF-BB, a growth factor of PASMCs, overexpressed in PAH thus overactivating the PDGFR and participating to vascular remodeling[37]. Interestingly, a crosstalk of NMDAR and PDGFR pathways is operating in neurons of the CNS, with PDGF stimulation modulating NMDAR activity and orientating NMDAR response to activation of proliferation-related MAPK and CREB signaling pathways[38,39]. Importantly, NMDAR antagonists MK-801 and MMT attenuated hPASMCs proliferation induced by PDGF-BB without adding any NMDAR agonists to the medium. Contrary to ET-1 stimulation, PDGF-BB did not further increase the basal release of glutamate from control hPASMCs suggesting a role in mobilizing NMDARs. Thus, we explored the potential of PDGF-BB to phosphorylate GluN1 in hPASMCs on Ser896, a site phosphorylated in pulmonary arteries of PAH patients. Kinetics analysis showed increased GluN1 phosphorylation after 10 min of PDGF-BB exposure and followed by a slight decrease after 30 min to 1 h. These results indicate that PDGF-BB could activate NMDAR trafficking, phosphorylating the obligatory GluN1 subunit within minutes, then contributing to proliferative effects. Thus, PDGF-BB and/or ET-1 could be responsible for the increased phosphorylation of GluN1 observed in situ in pulmonary arteries from PAH patients especially in PASMC, a cell type known to express abundantly the PDGFR. We conclude that NMDAR expressed by PASMC contributes to vascular remodeling, resulting in an increased RVSP and subsequently right cardiac hypertrophy in the hypoxic mice model. Moreover, PDGF-BB could mobilize NMDAR in order to participate to the resulting proliferative effect.

Activation of Endothelial NMDARs Contributes to the Vascular Remodeling Occurring During PH Development.

Figure 1F:
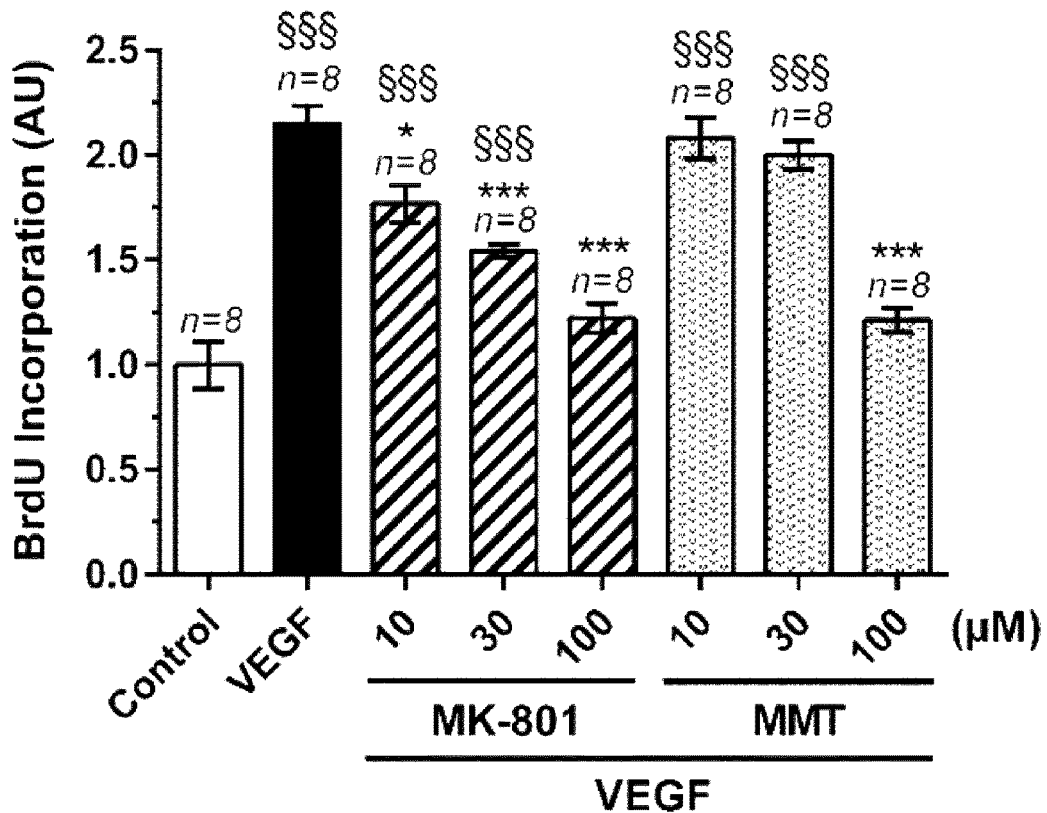
Figure 1G:
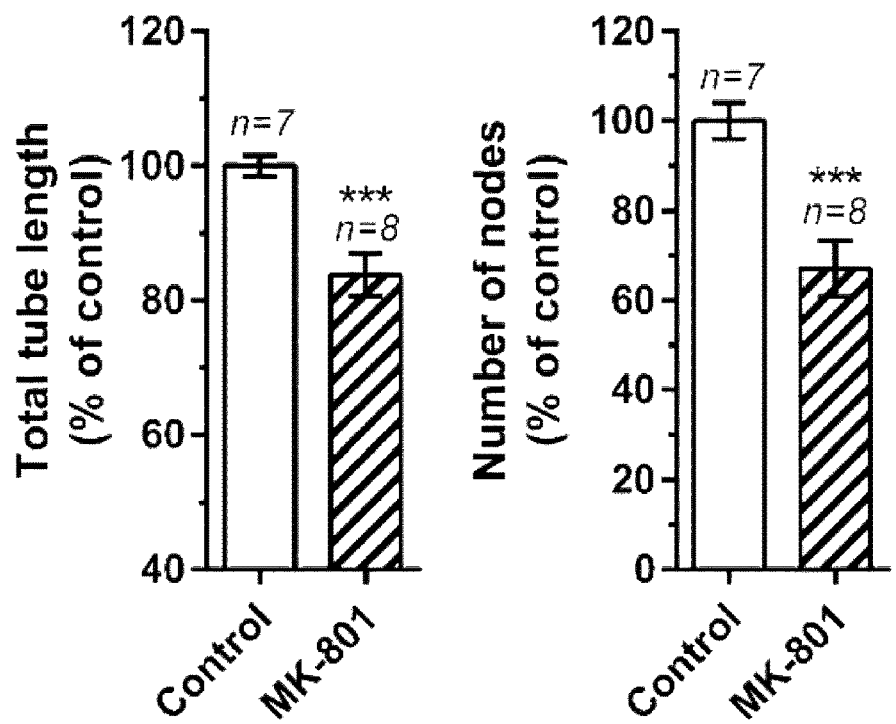
Figure 1H:
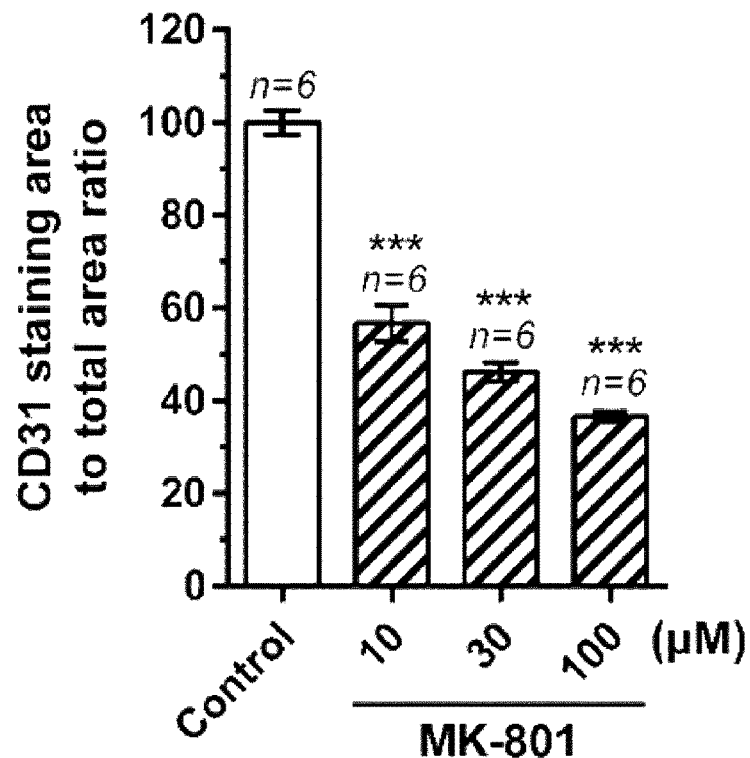
Figure 2G:
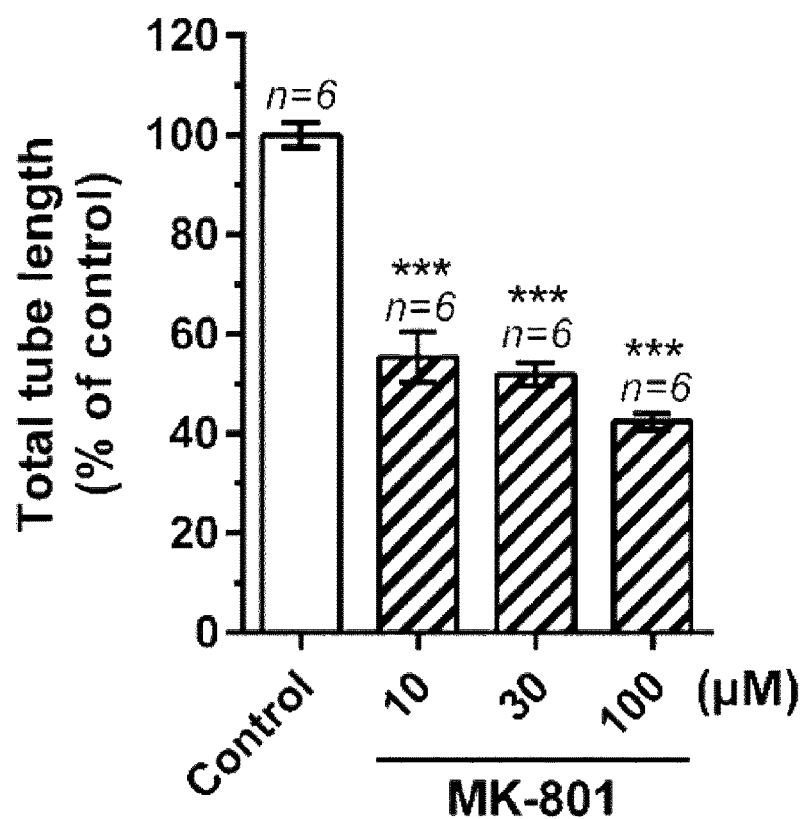

It has been suggested that NMDAR activation in CNS endothelial cell can disturb the endothelial barrier through production of reactive oxygen species, favor monocyte transmigration and induce proliferation[18-20,22]. As vascular remodeling associated to PAH involves breakdown of endothelial junctions, oxidant stress, proliferation and adventitial inflammation[40], we evaluated the participation of endothelial NMDARs in PAH development. Correlative light and electron microscopy, allowed investigating the number and the localization of NMDARs (precisely GluN1 protein) in pulmonary artery endothelial cells from a PH patient compared to control. We focused on an intimal and a plexiform lesion as they mainly depend on the endothelial layer dysfunction. Synaptic-like contact was defined as a close contact <70 μm between two endothelial cells without junctions. We show that the total number of immunogold particles per 100 µm² of endothelial cells (FIG. 2a), the partition/distribution between membrane and cytoplasmic GluN1 as well as the proportion of synaptic-like contact length relative to the total membrane length (FIG. 1a) did not change between the PAH artery compared to control artery. Importantly, membrane GluN1 located in these contact areas is increased in plexiform lesion compared to intimal lesion and control artery (29.5% of total membrane GluN1 in plexiform lesion vs 7.7% in intimal lesion and 4.1% in control artery). In the intimal lesion, membrane GluN1 proteins are 3.5 fold enriched inside/along synaptic-like contacts compared to the control artery. In plexiform lesion, this index even reaches 7.1 (FIG. 1a). These membrane-GluN1 proteins represent available NMDAR for activation that seems accumulated and/or concentrated inside/along synaptic-like contact between endothelial cells suggesting increased glutamatergic signaling between endothelial cells in PAH lesions. To explore the potential involvement of endothelial NMDAR in the vascular remodeling associated to PH we developed endothelial cell-targeted KO mice for Grin1 gene using tamoxifen-inducible Cre/Lox strategy. After tamoxifen administration, Grin1 gene expression was markedly reduced in CD31+ cells isolated from the lung of KO mice compared to WT mice suggesting efficient Grin1 gene recombination (FIG. 1b). These mice were exposed to normoxia or hypoxia for 3 weeks before measuring RVSP and calculating the Fulton index. No difference was observed in body weight although normoxic KO mice were slightly older than WT mice. In normoxic mice, no difference in RVSP or Fulton index between WT and KO mice was highlighted. After hypoxia, KO mice presented a decreased right cardiac hypertrophy and a decreased RVSP (FIG. 1c,d). Morphometric analysis of the pulmonary arteries revealed a significant decrease of the muscularization only in small arterioles (<50 µm external diameter) between WT and KO mice after chronic hypoxia (FIG. 1e). No difference was observed for larger arteries between WT and KO mice in both normoxia and hypoxia. As excessive endothelial cell proliferation and dysregulated angiogenesis are part of the vascular remodeling processes demonstrated in PAH plexiform lesions[41], and because VEGF signaling and NMDAR have been shown to cooperate in neurons in the CNS[42], we have investigated whether NMDAR activation could participate to endothelial cell proliferation and angiogenesis. NMDAR antagonists MK-801 and MMT dose-dependently inhibit hPMVEC proliferation stimulated either by FBS 10% or VEGF-A 10 ng·ml$^{-1}$ without adding exogenous NMDAR agonists (FIG. 1f, FIG. 2e). As VEGF is one of the main angiogenesis mediators, we have explored the hypothesis whether NMDAR activation is involved in angiogenesis. In the matrigel assay, MK-801 and the competitive NMDAR antagonist DAP-5 decrease total tube length formation and the number of nodes (FIG. 1g FIG. 2f). In a second in vitro angiogenesis assay based on hPMVECs and hPASMCs co-culture, MK-801 dose-dependently inhibits the formation of the endothelial tube network (FIG. 1h, FIG. 2g). We conclude that NMDAR is dysregulated in endothelial cells in PAH intimal and plexiform lesions and contributes to vascular remodeling. Moreover it participates to VEGF proliferation and angiogenesis.

Discussion

Using electron microscopy on human pulmonary tissues from PAH and control patient, we have observed a local concentration of NMDAR in synaptic-like contact between endothelial cells, especially in the plexiform lesion, a PAH-typical lesion characterized by disorganized and excessive angiogenesis in which increased VEGF signaling has been previously pointed out[41]. In cerebellar granule cells, VEGFR-2 physically interacts with NMDAR modulating its activity [42]. Here we have shown that NMDAR antagonists are able to dose-dependently inhibit VEGF-induced proliferation and angiogenesis. Intriguingly, expression of NMDAR-associated synaptic proteins neurologin and neurexin that trigger synapse formation in the CNS have already been described in vascular cells playing a role in angiogenesis[56] and common variants in cerebellin 2, a partner of neurexin and expressed by pulmonary endothelial cells, increases the risk of PAH by approximately two-fold[57].

REFERENCES

Throughout this application, various references describe the state of the art to which this invention pertains. The disclosures of these references are hereby incorporated by reference into the present disclosure.

5. Traynelis, S. F. et al. Glutamate Receptor Ion Channels: Structure, Regulation, and Function. Pharmacol. Rev. 62, 405-496 (2010).

6. Petralia, R. S. Distribution of Extrasynaptic NMDA Receptors on Neurons. Sci. World J. 2012, e267120 (2012).

7. Dong, X., Wang, Y. & Qin, Z. Molecular mechanisms of excitotoxicity and their relevance to pathogenesis of neurodegenerative diseases. Acta Pharmacol. Sin. 30, 379-387 (2009).

8. Barkus, C. et al. Hippocampal NMDA receptors and anxiety: At the interface between cognition and emotion. Eur. J. Pharmacol. 626, 49-56 (2010).

9. Wesseling, H. et al. Integrative proteomic analysis of the NMDA NR1 knockdown mouse model reveals effects on central and peripheral pathways associated with schizophrenia and autism spectrum disorders. Mol. Autism 5, 38 (2014).

10. Paoletti, P., Bellone, C. & Zhou, Q. NMDA receptor subunit diversity: impact on receptor properties, synaptic plasticity and disease. Nat. Rev. Neurosci. 14, 383-400 (2013).

11. Parsons, M. P. & Raymond, L. A. Extrasynaptic NMDA Receptor Involvement in Central Nervous System Disorders. Neuron 82, 279-293 (2014).

12. Nedergaard, M., Takano, T. & Hansen, A. J. Beyond the role of glutamate as a neurotransmitter. Nat. Rev. Neurosci. 3, 748-755 (2002).

13. Genever, P. G. & Skerry, T. M. Glutamate signalling in bone: a therapeutic target for osteoporosis? Expert Opin. Ther. Targets 4, 207-218 (2000).

14. Bozic, M. & Valdivielso, J. M. The potential of targeting NMDA receptors outside the CNS. Expert Opin. Ther. Targets 19, 399-413 (2014).

15. Marquard, J. et al. Characterization of pancreatic NMDA receptors as possible drug targets for diabetes treatment. Nat. Med. 21, 363-372 (2015).

16. Affaticati, P. et al. Sustained calcium signalling and caspase-3 activation involve NMDA receptors in thymocytes in contact with dendritic cells. Cell Death Differ. 18, 99-108 (2011).

17. Malomouzh, A. I., Nurullin, L. F., Arkhipova, S. S. & Nikolsky, E. E. NMDA receptors at the endplate of rat skeletal muscles: Precise postsynaptic localization. Muscle Nerve 44, 987-989 (2011).

18. Sharp, C. D. et al. Glutamate causes a loss in human cerebral endothelial barrier integrity through activation of NMDA receptor. Am. J. Physiol. Heart Circ. Physiol. 285, H2592-2598 (2003).

19. Sharp, C. D. et al. N-methyl-D-aspartate receptor activation in human cerebral endothelium promotes intracellular oxidant stress. Am. J. Physiol. Heart Circ. Physiol. 288, H1893-1899 (2005).

20. Reijerkerk, A. et al. The NR1 subunit of NMDA receptor regulates monocyte transmigration through the brain endothelial cell barrier. J. Neurochem. 113, 447-453 (2010).

21. András, I. E. et al. The NMDA and AMPA/KA receptors are involved in glutamate-induced alterations of occludin expression and phosphorylation in brain endothelial cells. J. Cereb. Blood Flow Metab. 27, 1431-1443 (2007).

22. Chen, H. et al. Identification of a homocysteine receptor in the peripheral endothelium and its role in proliferation. J. Vasc. Surg. 41, 853-860 (2005).

23. Parfenova, H. Glutamate induces oxidative stress and apoptosis in cerebral vascular endothelial cells: contributions of HO-1 and HO-2 to cytoprotection. AJP Cell Physiol. 290, C1399-C1410 (2005).

24. Beard, R. S., Reynolds, J. J. & Bearden, S. E. Hyperhomocysteinemia increases permeability of the blood-brain barrier by NMDA receptor-dependent regulation of adherens and tight junctions. Blood 118, 2007-2014 (2011).

25. Doronzo, G. et al. Role of NMDA receptor in homocysteine-induced activation of mitogen-activated protein kinase and phosphatidyl inositol 3-kinase pathways in cultured human vascular smooth muscle cells. Thromb. Res. 125, e23-32 (2010).

26. Moriyama, Y. & Yamamoto, A. Glutamatergic Chemical Transmission: Look! Here, There, and Anywhere. J. Biochem. (Tokyo) 135, 155-163 (2004).

27. Li, L. & Hanahan, D. Hijacking the neuronal NMDAR signaling circuit to promote tumor growth and invasion. Cell 153, 86-100 (2013).

28. Stepulak, A. et al. NMDA antagonist inhibits the extracellular signal-regulated kinase pathway and suppresses cancer growth. Proc. Natl. Acad. Sci. U.S.A. 102, 15605-15610 (2005).

29. Rzeski, W., Turski, L. & Ikonomidou, C. Glutamate antagonists limit tumor growth. Proc. Natl. Acad. Sci. U.S.A. 98, 6372-6377 (2001).

30. Guignabert, C. et al. Pathogenesis of pulmonary arterial hypertension: lessons from cancer. Eur. Respir. Rev. 22, 543-551 (2013).

37. Perros, F. et al. Platelet-derived growth factor expression and function in idiopathic pulmonary arterial hypertension. Am. J. Respir. Crit. Care Med. 178, 81-88 (2008).

38. Lei, S. et al. Platelet-derived growth factor receptor-induced feed-forward inhibition of excitatory transmission between hippocampal pyramidal neurons. J. Biol. Chem. 274, 30617-30623 (1999).

39. Beazely, M. A. et al. Platelet-derived Growth Factor Selectively Inhibits NR2B-containing N-Methyl-D-aspartate Receptors in CA1 Hippocampal Neurons. J. Biol. Chem. 284, 8054-8063 (2009).

41. Tuder, R. M. et al. Expression of angiogenesis-related molecules in plexiform lesions in severe pulmonary hypertension: evidence for a process of disordered angiogenesis. J. Pathol. 195, 367-374 (2001).

42. Meissirel, C. et al. VEGF modulates NMDA receptors activity in cerebellar granule cells through Src-family kinases before synapse formation. Proc. Natl. Acad. Sci. U.S.A. 108, 13782-13787 (2011).

56. Bottos, A. et al. The synaptic proteins neurexins and neuroligins are widely expressed in the vascular system and contribute to its functions. Proc. Natl. Acad. Sci. 106, 20782-20787 (2009).

The invention claimed is:

1. A method of inhibiting angiogenesis in a subject in need thereof comprising
administering to the subject an antagonist of N-Methyl-D-aspartate receptor (NMDAR) or an inhibitor of NMDAR expression.

2. The method of claim 1, wherein the antagonist of NMDAR is selected from the group consisting of:
 i. a small organic molecule;
 ii. an anti-NMDAR antibody or antibody fragment; and
 iii. a polypeptide.

3. The method of claim 1, wherein the inhibitor of NMDAR expression is a siRNA, a ribozyme, or an antisense oligonucleotide.

4. A method of treating tumor angiogenesis in a subject in need thereof comprising
administering to the subject an antagonist of N-Methyl-D-aspartate receptor (NMDAR) or an inhibitor of NMDAR expression, wherein the antagonist or the inhibitor inhibit angiogenesis.

5. The method of claim 4, wherein the antagonist of NMDAR is selected from the group consisting of:
 i. a small organic molecule;
 ii. an anti-NMDAR antibody or antibody fragment; and
 iii. a polypeptide.

6. The method of claim 4, wherein said inhibitor of NMDAR expression is a siRNA, a ribozyme, or an antisense oligonucleotide.

7. The method of claim 4, wherein the antagonist of NMDAR is selected from the group consisting of:
 i. a small organic molecule;
 ii. an anti-NMDAR antibody or antibody fragment; and
 iii. a polypeptide.

8. The method of claim 4, wherein the inhibitor of NMDAR expression is a siRNA, a ribozyme, or an antisense oligonucleotide.

* * * * *